US008155268B2

(12) United States Patent
Pesce et al.

(10) Patent No.: US 8,155,268 B2
(45) Date of Patent: Apr. 10, 2012

(54) RAPID SCREENING FOR LEAD CONCENTRATION COMPLIANCE BY X-RAY FLUORESCENCE (XRF) ANALYSIS

(75) Inventors: John Pesce, Melrose, MA (US); Lee Grodzins, Lexington, MA (US)

(73) Assignee: Thermo Niton Analyzers LLC, Billerica, MA (US)

( * ) Notice: Subject to any disclaimer, the term of this patent is extended or adjusted under 35 U.S.C. 154(b) by 179 days.

(21) Appl. No.: 12/766,250

(22) Filed: Apr. 23, 2010

(65) Prior Publication Data
US 2010/0272232 A1    Oct. 28, 2010

Related U.S. Application Data

(60) Provisional application No. 61/172,117, filed on Apr. 23, 2009.

(51) Int. Cl.
*G01N 23/223* (2006.01)
(52) U.S. Cl. ............................................ 378/45; 378/46
(58) Field of Classification Search .................... 378/42, 378/45, 46, 70, 83
See application file for complete search history.

(56) References Cited

U.S. PATENT DOCUMENTS

| | | | |
|---|---|---|---|
| 3,787,691 A | 1/1974 | Laurer | |
| 4,551,848 A | 11/1985 | Greenwood-Smith | |
| 4,845,729 A | 7/1989 | Rosen et al. | |
| 5,274,688 A | 12/1993 | Grodzins | |
| 5,390,229 A | 2/1995 | Grodzins | |
| 5,396,529 A | 3/1995 | Grodzins | |
| 5,461,654 A | 10/1995 | Grodzins et al. | |
| 6,349,128 B1 | 2/2002 | Nelson | |
| 6,765,986 B2 | 7/2004 | Grodzins et al. | |
| 7,302,034 B2 | 11/2007 | Grodzins | |
| 7,702,067 B2 * | 4/2010 | Grodzins et al. | 378/45 |
| 2008/0192889 A1 | 8/2008 | Rohde et al. | |

OTHER PUBLICATIONS

Kataoka, Yoshiyuki, "Standardless X-Ray Fluorescence Spectrometry," The Rigaku Journal, vol. 6 (1), 1989, pp. 33-39.
D.K.G. De Boer et al., "How Accurate is the Fundamental Parameter Approach? XRF Analysis of Bulk and Multilayer Samples," X-Ray Spectrometry, vol. 22 (1993), pp. 33-38.
Cesareo et al., "Giotto in the Chapel of the Scrovegni: EDXRF analysis of the golden haloes with portable equipment," X-Ray Spectrometry, vol. 33 (2004), pp. 289-293.
Ida et al., "Analysis of wrapped or cased object by a hand-held X-ray fluorescence spectrometer," Forensic Science International, vol. 151, No. 2-3 (2005), pp. 267-272.

* cited by examiner

*Primary Examiner* — Irakli Kiknadze
(74) *Attorney, Agent, or Firm* — Gordon Stewart

(57) ABSTRACT

A method is provided for screening lead concentration compliance of objects, particularly consumer products such as toys, using x-ray fluorescence (XRF) analysis. The measured intensity ratio of the characteristic $L_\alpha$ and $L_\beta$ x-rays of lead provides an indication of whether the lead is located primarily in a coating (e.g., paint) layer on the object, or in a thin or thick bulk material. If the intensity ratio indicates that the lead is located in a coating layer or distributed in a thin bulk material, an areal density of lead is determined from at least one of the characteristic x-ray intensities, and the measured areal density is compared to specified lower and upper limits to determine whether the object is unambiguously compliant, unambiguously non-compliant, or indeterminate.

5 Claims, 3 Drawing Sheets

RAPID SCREENING FOR LEAD CONCENTRATION COMPLIANCE BY X-RAY FLUORESCENCE (XRF) ANALYSIS

CROSS-REFERENCE TO RELATED APPLICATION

This application claims the priority benefit under 35 U.S.C. §119(e) of U.S. provisional application No. 61/172,117 entitled "Rapid Screening for Lead Concentration Compliance by X-Ray Fluorescence (XRF) Analysis", filed on Apr. 23, 2009, the entire disclosure of which is incorporated herein by reference.

FIELD OF THE INVENTION

The present invention relates generally to the measurement of elemental composition by x-ray fluorescence, and more particularly to a method for efficiently and quickly analyzing objects by x-ray fluorescence to assess compliance with relevant regulatory requirements for lead concentration.

BACKGROUND OF THE INVENTION

Lead has been known to be a toxic element for more than a century. In recent decades, scientists and the public have become aware of the harm lead does to children, producing severe adverse effects to their mental and behavioral abilities in direct proportion to the concentration level of lead in their bodies. Governments have regulated the maximum concentration of lead in paint and in the bulk materials of consumer goods in order to protect the safety of the public, prevent the build up of toxic elements in waste disposals, and prevent its reuse in recycling.

In the Consumer Product Safety Improvement Act of 2008 (CPSIA), signed into law Aug. 14, 2008, the U.S. regulations were revised significantly. The older regulations required that the concentration of lead, in either the bulk of the material or the paint on the material, can be no greater than 600 parts per million; that is, that there must not be more than 600 µg of lead in each gram of either the bulk material or the paint on it. The new regulations have reduced the weight concentration of either bulk or paint to 90 ppm. The regulations allow the examination of small areas of paint (less than 10 milligram (mg) in weight) to be examined by x-ray fluorescence to meet a requirement that the areal density of the lead, that is, the weight in a square centimeter of paint (alternatively referred to as the mass thickness), be no greater than 2 µg/cm². The CPSIA was a result of public demand for better consumer safety after the discovery that a significant number of toys had levels of lead that far exceeded the previously existing regulations.

The challenge for maintaining public safety is how to enforce the regulations when most of the billions of the toys and consumer products are imported from countries that have minimal supervision of the production of the bulk material or the paint. Making the problem even more difficult is that the new regulations continue to be based on the weight concentration of the lead, which is an appropriate measure for raw material but perhaps not for finished goods. The measurement of the weight concentration of the lead is by definition the measurement of the weight of the lead in a known weight of the bulk or the paint. Measuring the weight percent of lead in paint on a toy, for example, requires scraping off a paint chip, measuring its weight and then measuring the lead concentration at a certified laboratory using such techniques as inductively-coupled plasma optical emission spectroscopy (ICP-OES), inductively-coupled plasma mass spectrometry (ICP-MS), or flame atomic emission spectroscopy. These techniques are generally destructive, time-consuming and expensive.

Several references in the prior art (see, e.g., U.S. Patent Application Publication No. 2009/0067572 by Grodzins et al.) have demonstrated the ability of XRF instruments to distinguish between surface lead (i.e., lead present primarily in the paint or other coating layer) and bulk lead (i.e., lead distributed through the bulk thickness). Once the location of the lead is identified, its concentration may be calculated using location-specific algorithms. However, accurate calculation of the lead content by the disclosed techniques may require prior knowledge of the construction of the inspected object and/or prolonged irradiation/analysis times. For testing of consumer products, such as toys, information regarding the construction of the object to be inspected may not be available to the operator, potentially compromising the accuracy of the measurements. Furthermore, it is generally desirable to minimize the required time for analysis in order to increase testing throughput and reduce overall costs. Against this background, there is a need for an accurate lead concentration testing method that may be administered relatively quickly and inexpensively.

SUMMARY

Roughly described, embodiments of the present invention provide methods for rapid screening of objects for lead concentration compliance by XRF analysis, enabling an operator to easily and quickly identify, without prior knowledge of an object's construction, whether an inspected object is unambiguously compliant or non-compliant with regulatory or other relevant standards. Objects that cannot be determined to be unambiguously compliant or non-compliant (which will typically comprise a very small fraction of the total number of inspected objects) can be set aside and subjected to laboratory testing, such as ICP-OES, for more definitive analysis and classification.

According to various embodiments, the object to be tested is irradiated with a primary beam of x-rays having energies suitable for causing lead atoms present in the object to fluoresce at characteristic wavelengths, including the well-known $L_\alpha$ and $L_\beta$ x-rays. The x-rays emitted from the object are received by a detector, which responsively generates signals representative of the x-ray energies. These signals are accumulated and processed by a controller to calculate the intensities (e.g., in counts/unit time) of the received x-rays.

The location of the lead within the object is determined based on the $L_\alpha/L_\beta$ intensity ratio. If the ratio indicates that the lead is located in thick bulk material, an appropriate technique (e.g., fundamental parameters) is invoked to determine the lead concentration as a weight concentration, which may be used to assess compliance. If, however, the ratio indicates that the lead is present primarily in a coating layer or in thin bulk material, the regulatory compliance is assessed based on the areal density, which may be determined from the measured intensities of the $L_\alpha$ and $L_\beta$ x-rays using empirical calibrations. Lower and upper areal density limits are then set depending on whether the $L_\alpha/L_\beta$ intensity ratio indicates that the lead is present primarily in the coating layer or distributed in a thin bulk layer. These areal density limits are determined based on the relationship between areal density and volumetric concentration and practical limits on the thickness of the lead-containing material layer. If the measured areal density is less then the lower limit, the object is classified as compliant. If the measured areal density is greater than the upper limit, then the object is classified as non-compliant. Finally, if the measured areal density lies between the lower and upper limits, the object is classified as indeterminate, indicating the need for further testing. The classification of the inspected object (compliant, non-compliant, or indeterminate) may then be displayed to the operator and/or recorded, such that the operator may take the appropriate action.

DETAILED DESCRIPTION OF EMBODIMENTS

Preferred embodiments of the invention are described below in connection with the FIG. 1 XRF analyzer and the method depicted in the FIG. 2 flowchart. It will be understood that the embodiments and examples discussed below are intended to illustrate rather than to limit the invention.

Figure 1:
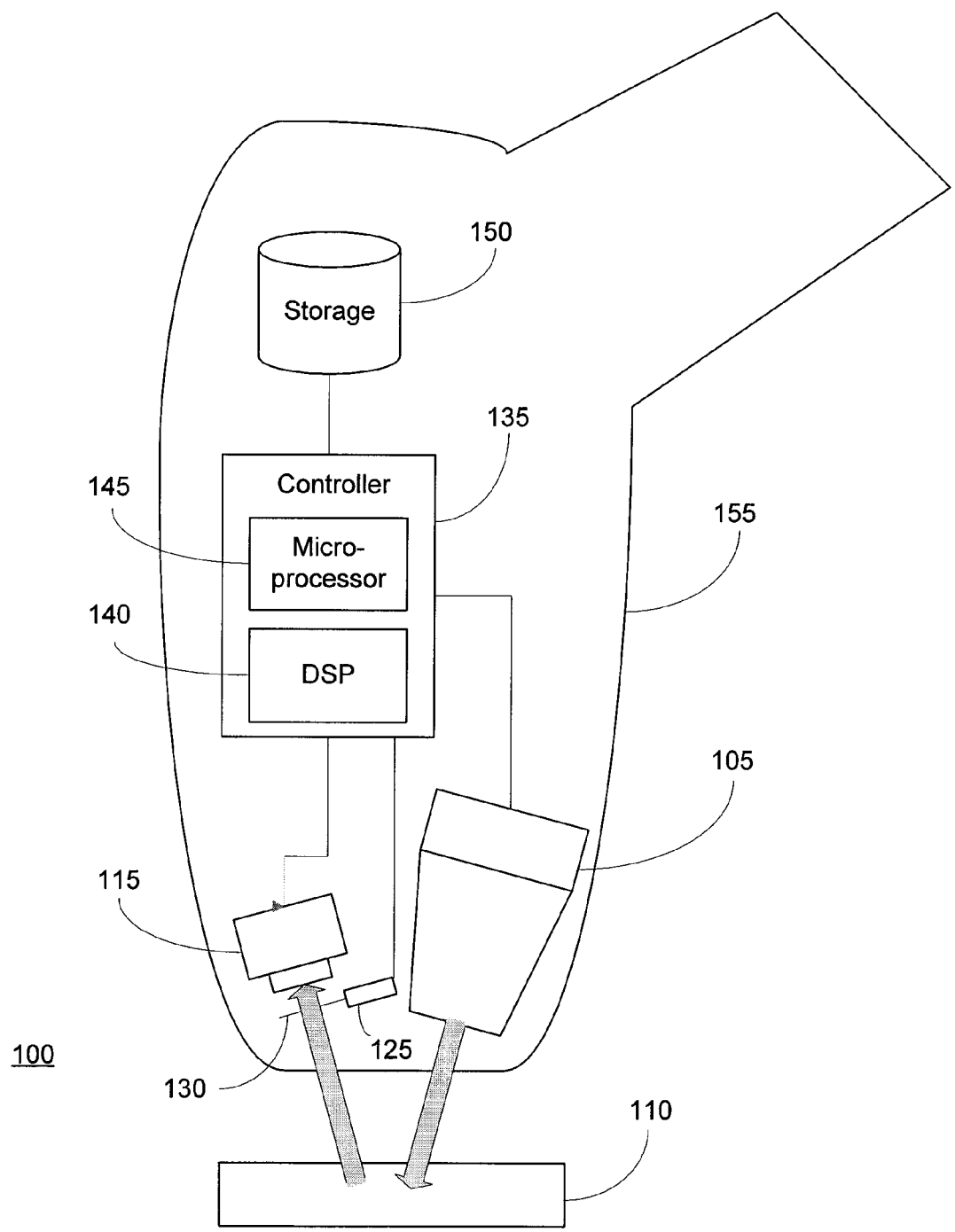
FIG. 1 is a symbolic diagram of an XRF analyzer.

FIG. 1 is a symbolic diagram of the components of an XRF analyzer 100 in which the fast screening techniques of the present invention may be advantageously implemented. XRF analyzer 100 includes an x-ray source 105 for generating a primary radiation beam to excite lead atoms in sample 110. X-ray source 105 may take the form of any suitable x-ray tube or radioisotope source. As used herein, the term "x-ray" is broadly defined to include any radiation having an energy suitable for causing fluorescence of the element of interest (i.e., lead) via ejection of an inner shell electron, and may encompass radiation classified as gamma-rays in other contexts. One or more not-depicted structures, such as filters, concentrators and collimators, may be positioned in the primary x-ray beam to tailor the energetic and/or geometric parameters of the x-ray beam so as to optimize the analyzer performance for specific applications.

Detector 115 is positioned to receive radiation emitted by sample 110. The emitted radiation will typically comprise a mixture of fluorescent x-rays characteristic of specific elements in sample 110 and elastically scattered (Rayleigh) and inelastically scattered (Compton) x-rays. The design and operation of XRF detectors are well known in the art and hence will not be discussed herein. Generally described, detector 115 generates a signal pulse in response to reception of an x-ray photon, the size of the pulse being representative of the photon's energy. Detector 115 may incorporate or have associated therewith preamplifier circuitry for integrating and amplifying current produced by the detector 115 crystal. In various implementations, detector 115 may take the form of a silicon PIN detector, cadmium telluride detector, or silicon drift detector.

A filter apparatus 125 may be provided to selectively position a filter 130 in the path of the radiation emitted by sample 110, such that x-rays of undesirable energies are preferentially absorbed or otherwise attenuated before the radiation reaches detector 115. Filter apparatus 125 may include a single filter that is controllably moveable between a first position that intersects the emitted radiation path, and a second position in which the filter is located outside of the emitted radiation path. In an alternative implementation, filter apparatus 125 includes a rotatable filter wheel having two or more filters of differing compositions and/or thicknesses.

The output of detector 115 is conveyed to programmable controller 135, which will typically incorporate at least one digital signal processor (DSP) 140 configured to amplify, process and accumulate the signal pulses such that an energy spectrum of the detected radiation may be constructed. As is known in the art, DSP 140 may execute routines for attenuating signals generated by detector 115 arising from various sources of noise. Programmable controller 135 may also include a specialized or general purpose microprocessor 145 for executing program instructions relating to data acquisition and analysis and instrument control, including implementations of the method steps depicted in FIG. 2 and discussed below. The program instructions executed by DSP 140 and microprocessor 145 may be stored in hardware, firmware or software logic form within controller 135 and/or non-volatile storage 150 coupled to controller 125. Storage 150 may also hold test results and information input by the operator.

The various components of XRF analyzer 100 may be located within a common housing 155 designed to be handheld by the operator. A touch screen display (not depicted) may be incorporated into or mounted to housing 155 to present text and graphics (e.g., representing analysis results) and to accept operator input. XRF analyzer 100 will typically include a wired (e.g., USB) or wireless (e.g., 802.11g) communications port to enable the uploading and downloading of analysis results, software, and other information to and form an external computer. In alternative implementations, certain of the components of XRF analyzer 100 may be located remotely from each other, e.g., components of controller 135 may reside on a general purpose computer that communicates with the other components over a wired or wireless connection.

XRF analyzers of the foregoing description are commercially available from various suppliers, such as the Niton® XL3t XRF analyzer manufactured by the Thermo Niton Analyzers division (Billerica, Mass.) of Thermo Fisher Scientific Inc.

Figure 2:
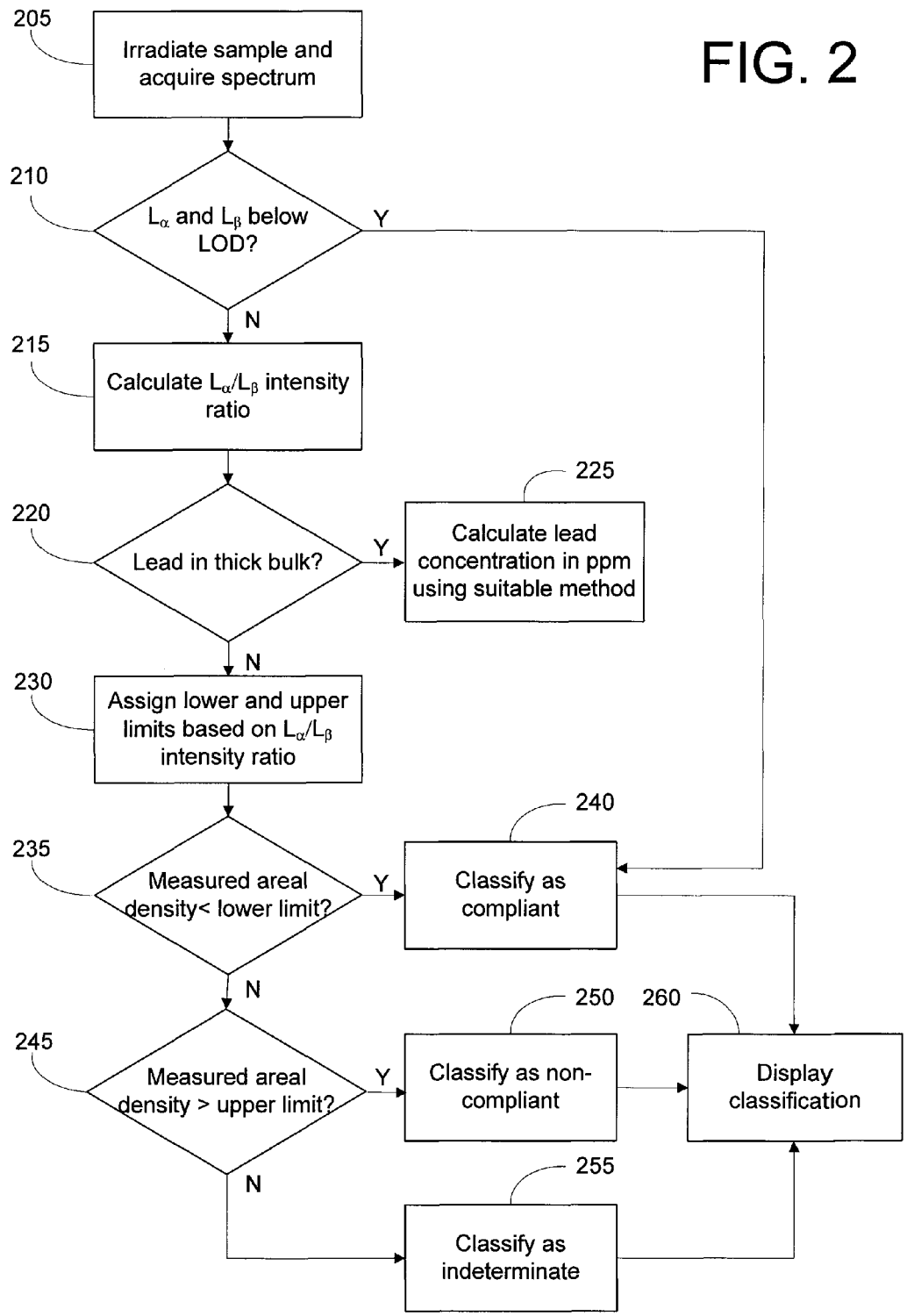
FIG. 2 is a flowchart depicting steps of a method of screening objects for lead concentration compliance using an XRF analyzer, in accordance with an illustrative embodiment of the invention.

FIG. 2 shows the steps of a method for operating an XRF analyzer to determine whether inspected object 110 complies with applicable lead concentration regulations. It should be noted that although the steps are presented in a particular order in the flowchart, certain of the steps will typically be conducted concurrently rather than sequentially, and so the flowchart should not be regarding as imposing a specifically ordered sequence of steps.

In step 205, a beam of primary x-ray radiation is directed unto the sample, e.g., by operation of x-ray source 105. This step may be initiated by operator action, such as be depressing a trigger mounted to housing 155. The operation of x-ray source 105 is preferably directed by controller 135, and certain of the beam parameters, such as intensity, energy and geometry, may be selected or adjusted based on operator input, for example by specifying the class or type of material.

A portion of the radiation emitted by sample 110, including fluoresced and scattered radiation, is received by detector 115 in step 205. As discussed above, detector 115 produces a series of pulses responsive to the reception of radiation, with each pulse being representative of the energy of a detected x-ray.

Controller 135 receives pulses generated by detector 115, and DSP 140 processes and accumulates the pulses over an analysis time to construct an energy spectrum, from which the intensities of the various x-ray peaks of interest may be determined. The total analysis time, i.e., the period over which the sample is irradiated and the emitted radiation is detected and processed, may be controlled by the operator, set to a fixed value, or may be adjusted based on evaluation of the energy spectrum as it is acquired (e.g., terminating the analysis when a specified number of counts have been detected, or when a targeted signal-to-noise ratio has been achieved). As noted above, the resultant energy spectrum contains one or more characteristic emission peaks of lead and/or other element of interest (e.g., the $L_\alpha$ and $L_\beta$ x-rays of lead, having respective energies of 10.5 keV and 12.6 keV), as well as characteristic emission peaks of other elements in the sample, and peaks corresponding to coherently and incoherently scattered radiation.

If the summed intensities of the $L_\alpha$ and $L_\beta$ x-ray peaks fall below the limit of detection (LOD) of the XRF instrument being employed, the object may be classified as compliant, step 210. Generally, the LOD will depend on the instrument design and operating parameters; in a typical commercial instrument and at typical operating parameters, measured $L_\alpha$ and $L_\beta$ x-ray intensities falling below the LOD will provide an unambiguous determination that the lead concentration of the inspected object is less than the maximum concentration prescribed by the applicable regulatory standard.

Assuming that the intensities exceed the LOD (as determined in step 210), the intensity ratio of the $L_\alpha$ and $L_\beta$ x-rays of lead is calculated. The value of the intensity ratio (represented herein as $I_{L\alpha}/I_{L\beta}$) provides an indication of where in the object the lead is primarily located, i.e., in a paint or other coating layer, in a thin bulk material, or in a thick bulk material. An $I_{L\alpha}/I_{L\beta}$ value of less than about 1.0 provides an unambiguous indication that the lead is located in a thick bulk material. If the thick bulk material $I_{L\alpha}/I_{L\beta}$ criterion is satisfied in step 220, then the lead concentration in the inspected object is determined as a weight concentration (e.g., in parts per million, or ppm) from the acquired energy spectrum using a suitable technique such as fundamental parameters (FP), step 225. The FP technique, which is derived from the theoretical relationship between measured x-ray intensities and the concentrations of elements in the inspected object is well known in the XRF art for the determination of the elemental composition of an inspected object and hence need not be discussed herein.

If the value of $I_{L\alpha}/I_{L\beta}$ does not provide an unambiguous indication that the lead is located primarily in a thick bulk material (e.g., has a value of greater than about 1.0), then the method proceeds to step 230 for the assignment of lower and upper areal density limits. These areal density limits are utilized in subsequent steps for compliance classification of the inspected object. The areal density limit values are set on the basis of $I_{L\alpha}/I_{L\beta}$, as well as information regarding the regulatory requirements and the practical constraints on thickness of material in consumer goods, as described below.

Regulatory limits for lead in consumer goods are commonly expressed as weight concentrations; for example, the previously discussed U.S. CPSIA sets a weight concentration limit of 90 ppm for lead present in either the coating or bulk. The areal density, in units of $\mu g/cm^2$ is related to the weight concentration of lead $C_{Pb}$ (expressed in units of ppm or $\mu g/g$) by the density $\rho$ (in units of $g/cm^3$) and the thickness T (in units of cm) of the measurement volume, as given by the following equation.

$$ArealDensity = C_{Pb} * \rho * T$$

We demonstrate below how the regulatory weight concentration limit, in ppm, may be translated into areal density parameters using the above equation and known practical constraints.

Figure 3:
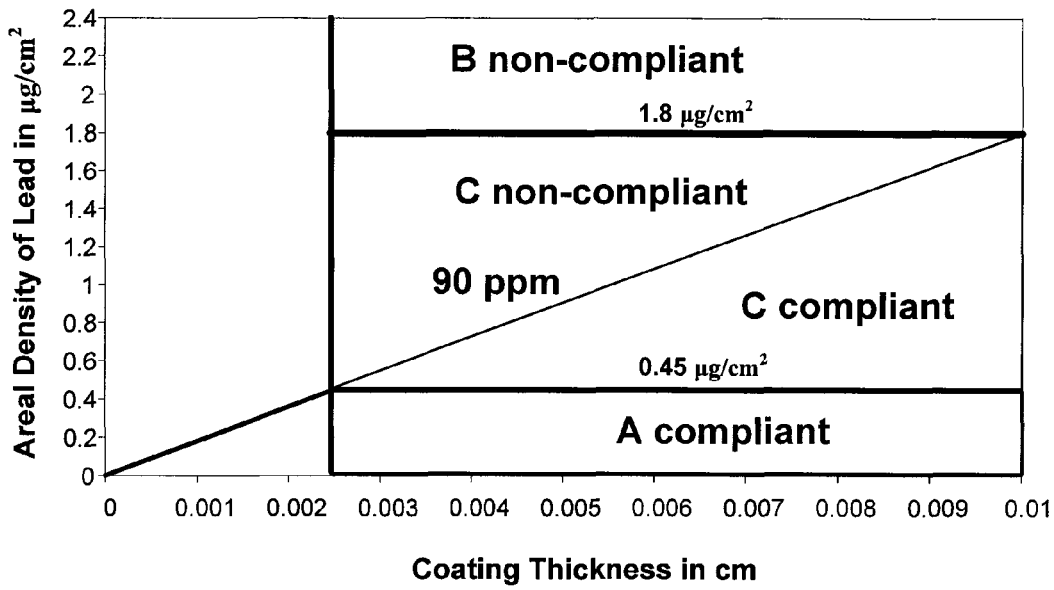
FIG. 3 is a graph depicting regions of regulatory compliance and non-compliance based on the relationship between areal density and volumetric concentration of lead contained in a coating layer.

FIG. 3 is a graph depicting regions of regulatory compliance and non-compliance based on the relationship between areal density and weight concentration of lead contained primarily in a coating layer. Coating layers on consumer products, which typically take the form of paint, are known to be applied to a thickness T of between 1-4 mils (0.0025-0.01 cm), and to have a density $\rho$ of about 2.0 $g/cm^3$. At these conditions, the lead $L_\alpha$ and $L_\beta$ x-rays emanating from this range of paint are not appreciably absorbed, and the intensity ratio $I_{L\alpha}/I_{L\beta}$ is therefore about 1.2, which is the ratio in which the $L_\alpha$ and $L_\beta$ x-rays are emitted by lead atoms in response to the fluorescing radiation. Thus, if it is determined in step 215 that $I_{L\alpha}/I_{L\beta}$ is approximately 1.2, the method assumes that the detected lead is present primarily in the coating layer, and relies on this assumption to set the areal density limits for assessment of compliance, as set forth below.

In FIG. 3, the diagonal line represents the 90 ppm weight concentration limit imposed by the CPSIA. Values of areal density for lead that lie below this line are compliant with the regulatory standard, while values above this line are non-compliant. It is discernible that for all values of coating thickness within the range of practicality (0.0025-0.01 cm), a measured areal density of less than 0.45 $\mu g/cm^2$ will be compliant with the 90 ppm standard. Thus, the 0.45 $\mu g/cm^2$ value defines a lower areal density limit below which measured areal densities will be deemed compliant, as indicated by compliant region A. Conversely, a measured areal density above 1.8 $\mu g/cm^2$ will be non-compliant with the 90 ppm standard for all practical coating thickness values, such that the 1.8 $\mu g/cm^2$ value defines an upper areal density limit above which measured areal densities will be deemed non-compliant, as indicated by compliant region B. Measured areal densities that lie between the lower and upper areal density limits (indicated on the graph as region C) may or may not be compliant with the 90 ppm standard, depending on the coating thickness, and thus objects having measured areal densities that lie between the lower and upper areal density limits (i.e., between 0.45 and 1.8 $\mu g/cm^2$) are classified as indeterminate, since their coating thicknesses are not known.

Figure 4:
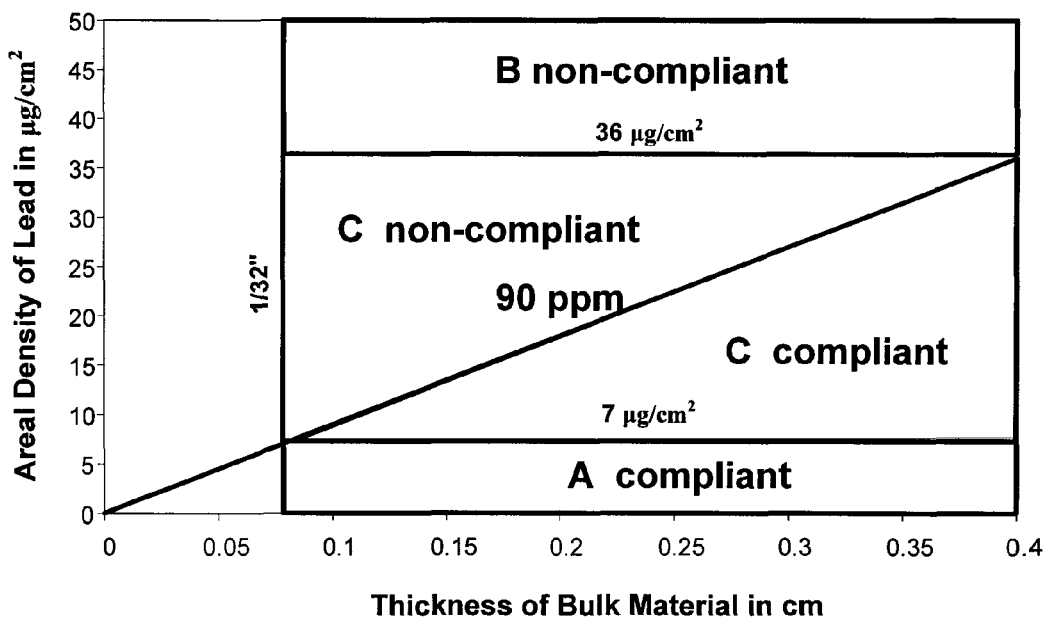
FIG. 4 is a graph depicting regions of regulatory compliance and non-compliance based on the relationship between areal density and volumetric concentration of lead contained in a thin bulk material.

If the value of $I_{L\alpha}/I_{L\beta}$ determined in step 215 indicates that the fluoresced $L_\alpha$ and $L_\beta$ x-rays emanate from lead distributed in a thin bulk material, i.e., if $I_{L\alpha}/I_{L\beta}$ is less than about 1.2 (resulting from the preferential attenuation of $L_\alpha$ x-rays), then the determination of the upper and lower areal density limits proceeds as follows. FIG. 4 is a graph depicting regions of regulatory compliance and non-compliance based on the relationship between areal density and weight concentration of lead contained primarily in a thin bulk layer. It is a reliable assumption that the thin bulk material of a consumer product is composed of a plastic having a density of about 1.0 $g/cm^3$. Depicted on FIG. 4 are two vertical lines corresponding to thicknesses of 0.075 cm (~1/32") and 0.4 cm. The first value of 0.075 cm represents a structural constraint; thinner plastic is generally not sufficiently strong for use in consumer products. The second value of 0.4 cm represents the transition to a "thick" bulk material, as greater thicknesses of bulk material attenuate the $L_\alpha$ x-rays to a degree sufficient to satisfy the "thick bulk" criterion in step 220 and thereby trigger the calculation of the weight concentration of lead in the object in accordance with step 225.

FIG. 4 shows that for all values of bulk material thickness within the range of practicality (0.0025-0.01 cm) for "thin bulk" materials, a measured areal density of less than 7 $\mu g/cm^2$ will be compliant with the 90 ppm standard. The 7 $\mu g/cm^2$ value thus defines a lower areal density limit below which measured areal densities will be deemed compliant, as indicated by compliant region A. Conversely, a measured areal density above 36 $\mu g/cm^2$ will be non-compliant with the 90 ppm standard for all practical thickness values, such that the 36 $\mu g/cm^2$ value defines an upper areal density limit above which measured areal densities will be deemed non-compliant, as indicated by compliant region B. Measured areal densities that lie between the lower and upper areal density limits (indicated on the graph as region C) may or may not be compliant with the 90 ppm standard, depending on the coating thickness, and thus objects having measured areal densities that lie between the lower and upper areal density limits (i.e., between 7 and 36 $\mu g/cm^2$) are classified as indeterminate, since their bulk thicknesses are not known.

As noted above, the upper and lower areal density limits employed to assess compliance may be based on the relevant regulatory standards, typically expressed as a maximum concentration by weight. Alternatively, the upper and lower areal density limits may be based on an industry or other standard different from (e.g., more stringent than) the relevant regulatory standard. The standard to be used for calculation of the appropriate lower and upper areal density limits may be specified or input by the operator, for example via a user interface presented on a touch screen display of the XRF instrument.

The measured lead areal density of the inspected object is then compared to the lower and upper areal density limits set in step 230 to assess the compliance status of the inspected object, as depicted in steps 235 and 245. The measured lead areal density may be determined from one or both of the intensities of the detected $L_\alpha$ and $L_\beta$ x-rays of lead using a set of empirically derived calibration curves, in the manner well known in the art. If the measured areal density is less than the lower areal density limit, then the object is classified as compliant, step 240. If the measured areal density exceeds the upper areal density limit, then the object is classified as non-compliant, step 250. Finally, if the measured areal density falls between the lower and upper limits, then the object is classified as indeterminate, step 255.

In step 260, the determined classification of the inspected object is displayed (e.g., on a screen integrated into XRF analyzer 100) or otherwise indicated (for example audibly) to the operator. The classification may also be stored as a record in the analyzer memory for later review and compilation of statistics. If the inspected object is classified as indeterminate, then it may be set aside by the operator for more definitive testing at a laboratory, for example by a destructive technique such as ICP-OES.

In certain implementations, the method may include automatically re-measuring the lead areal density of the inspected object if the inspected object is classified as indeterminate based on an initially measured areal density that lies close to (i.e., is within a specified window of) the upper or lower areal density limit. The re-measurement of areal density may be performed with a longer irradiation/acquisition time in order to provide a more accurate determination of areal density. If the subsequent re-measurement shows that the areal density exceeds the upper areal limit or is less than the lower areal density limit, the inspected object may be re-classified (respectively) as non-compliant or compliant, thereby reducing the number of objects for which ICP-OES or other laboratory testing is required.

It is estimated by the inventors that the foregoing method, when used for lead concentration compliance testing of toys or other consumer goods, will unambiguously classify as compliant or non-compliant a large majority of the inspected objects, and thus dramatically lessen the time and cost associated with such testing. This method is particularly useful for the inspection of toys and other products manufactured from polyethylene and other plastic materials, which tend to exhibit intensity ratios in a range that renders difficult or unreliable XRF analysis techniques known in the art.

Those skilled in the art will recognize that the methods disclosed herein for rapid lead concentration screening may be easily extended to screening for other elements (e.g., cadmium) that are detectable by XRF analysis and which are or may become subject to regulatory limits.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inspecting an object by x-ray fluorescence for lead concentration compliance, comprising:
   irradiating the object with x-rays having energies suitable for causing lead present in the object to fluorescently emit characteristic $L_\alpha$ and $L_\beta$ x-ray radiation;
   measuring the intensities of the $L_\alpha$ and $L_\beta$ radiation emitted by the object;
   assigning lower and upper areal density limits based on a ratio of the intensities of the $L_\alpha$ and $L_\beta$ radiation;
   determining a measured areal density from at least one of the intensities of the $L_\alpha$ and $L_\beta$ radiation;
   classifying the object as one of compliant, non-compliant or indeterminate by comparing the measured areal density to the lower and upper areal density limits; and
   displaying the classification.

2. The method of claim 1, wherein the lower and upper density limits are assigned a first set of values if the $L_\alpha/L_\beta$ intensity ratio is about 1.2 and are assigned a second set of values if the $L_\alpha/L_\beta$ intensity ratio is less than about 1.2.

3. The method of claim 1, wherein a mass concentration of lead is determined if the $L_\alpha/L_\beta$ intensity ratio is less than about 1.0.

4. The method of claim 1, further comprising a step of re-measuring the intensities of the $L_\alpha$ and $L_\beta$ radiation emitted by the object if the measured areal density is within a window of the lower or upper areal density limit.

5. An x-ray fluorescence analyzer, comprising:
   an x-ray source for generating x-rays having energies suitable for causing lead present in an inspected object to fluorescently emit characteristic $L_\alpha$ and $L_\beta$ x-ray radiation;
   a detector positioned to receive the fluorescently emitted x-rays from the inspected object, and to responsively produce signals representative of the energies of the received x-rays;
   a controller, coupled to the detector, having logic for measuring the intensities of the $L_\alpha$ and $L_\beta$ radiation emitted by the object, assigning lower and upper areal density limits based on a ratio of the intensities of the $L_\alpha$ and $L_\beta$ radiation, determining a measured areal density from at least one of the intensities of the $L_\alpha$ and $L_\beta$ radiation, and classifying the object as one of compliant, non-compliant or indeterminate by comparing the measured areal density to the lower and upper areal density limits; and
   a display for displaying the classification.

* * * * *